(12) United States Patent
Zaid et al.

(10) Patent No.: US 12,053,440 B2
(45) Date of Patent: Aug. 6, 2024

(54) INHIBITION OF COVID-19 VIRUS BY FORMULATIONS CONTAINING CURCUMIN, HARMINE, AND ISOVANILLIN

(71) Applicant: Ankh Life Sciences Limited, Dublin (IE)

(72) Inventors: Gene H. Zaid, Hutchinson, KS (US); Cameron E. West, Sterling, KS (US); Robert Preston Moore, Great Bend, KS (US); Jason H. West, Hutchinson, KS (US)

(73) Assignee: Ankh Life Sciences Limited, Dublin (IE)

( * ) Notice: Subject to any disclaimer, the term of this patent is extended or adjusted under 35 U.S.C. 154(b) by 80 days.

(21) Appl. No.: 17/559,445

(22) Filed: Dec. 22, 2021

(65) Prior Publication Data

US 2022/0193007 A1 Jun. 23, 2022

Related U.S. Application Data

(60) Provisional application No. 63/129,428, filed on Dec. 22, 2020.

(51) Int. Cl.
*A61K 31/12* (2006.01)
*A61K 31/11* (2006.01)
*A61K 31/437* (2006.01)
*A61P 31/14* (2006.01)

(52) U.S. Cl.
CPC .............. *A61K 31/12* (2013.01); *A61K 31/11* (2013.01); *A61K 31/437* (2013.01); *A61P 31/14* (2018.01)

(58) Field of Classification Search
CPC .................................. A61K 31/12; A61P 31/14
See application file for complete search history.

(56) References Cited

U.S. PATENT DOCUMENTS

| | | | |
|---|---|---|---|
| 8,039,025 B1 | 10/2011 | Zaid et al. | |
| 9,402,834 B2 | 8/2016 | Zaid et al. | |
| 10,092,550 B2 * | 10/2018 | Zaid | A61K 31/4375 |
| 10,772,347 B2 | 9/2020 | Zaid et al. | |
| 2013/0165470 A1 | 6/2013 | Isfort et al. | |
| 2013/0309238 A1 | 11/2013 | Mattes et al. | |
| 2017/0042867 A1 * | 2/2017 | Zaid | A61K 47/10 |
| 2017/0216222 A1 * | 8/2017 | Zaid | A61K 31/11 |
| 2019/0231756 A1 | 8/2019 | Zaid et al. | |
| 2019/0269166 A1 | 9/2019 | Zaid et al. | |
| 2022/0175868 A1 | 6/2022 | Zaid et al. | |
| 2022/0175869 A1 | 6/2022 | Zaid et al. | |
| 2022/0193007 A1 | 6/2022 | Zaid et al. | |

FOREIGN PATENT DOCUMENTS

WO 2021191864 A1 9/2021

OTHER PUBLICATIONS

Van Sickle et al., Lipids, vol. 27, No. 3, pp. 157-160, 1992.*
Manoharan et al., Curcumin: a Wonder Drug as a Preventive Measure for COVID19 Management, Indian J Clin Biochem. Jul. 2020; 35(3): 373-375.*
Shen et al., High-Throughput Screening and Identification of Potent Broad-Spectrum Inhibitors of Coronaviruses, J Virology, Jun. 2019, vol. 93, Issue 12, 10.1128/jvi.00023-19.*
Booth et al., GZ17-6.02 initiates DNA damage causing autophagosome-dependent HDAC degradation resulting in enhanced anti-PD1 checkpoint inhibitory antibody efficacy, J Cell Physiol. Nov. 2020;235(11):8098-8113.*
Manoharan et al. "Curcumin: a Wonder Drug as a Preventive Measure for COVID19 Management." Ind J Clin Biochem (Jul.-Sep. 2020) 35(3): 373-375; Published online Jun. 17, 2020.
Naseri et al. "The Antiviral Effects of Curcumin Nanomicelles on the Attachment and Entry of Hepatitis C Virus." Iranian J Virol 2017:11(2): 29-35.
Roshdy et al. "EGYVIR: An immunomodulatory herbal extract with potent antiviral activity against SARS-CoV-2." PLoS ONE 15(11): e0241739. Published Nov. 18, 2020.
International Search Report and Written Opinion dated Mar. 9, 2022, in corresponding PCT/US2021/064888.
ThoughtCo, (https:www.thoughco.com/lyophilization-preserving-biological-material-375590) Jul. 15, 2019.
Wei, et al., "Beta-Sitosterol Solubility in Selected Organic Solvents", J Chem. Eng. Data, 2010, 55, 2917-2919.
Farid, et al., "Phytochemical constituents of the butanol fraction of Arum palaestinum Boiss.: cytotoxic and antiviral screening", JME, 2017, 8(7), 2585-2591.
Khan, et al., "Beta-Sitosterol: As Immunostimulant, Antioxidant and Inhibitor of SARS-CoV-2 Spike Glycoprotein", Scientific Archives, 2020, 2(1), 5 pages.
Said, et al., "Ethnopharmacological survey of medicinal herbs in Israel, the Golan Heights and the West Bank region", J Ethnopharm., 2002, 83, 251-265.
Bramwell, "A diverse history and a bright future", Natural Medicine Journal, 2019, 15 pages.
Iranshahy, et al., "Chemical composition and antibacterial properties of *Peganum harmala* L", Avicenna Journal of Phytomedicine, 2019, 9(6), 530-537.
Wink, "Potential of DNA Intercalating Alkaloids and OtherPlant Secondary Metabolites against SARS-CoV-2 Causing COVID-19", Diversity, 2020, 12, 175, 10 pages.
Shanmugarajan, et al., "Curcumin to inhibit binding of spike siycoprotein to ACE2 receptors: computational modelling, simulations, and ADMET studies to explore curcuminoids against novel SARS-COV-2 targets", RSC Adv., 2020, 10, 31385-31399.

(Continued)

Primary Examiner — Svetlana M Ivanova
(74) Attorney, Agent, or Firm — Hovey Williams LLP; Crissa A. Cook (57) ABSTRACT

The treatment of human subjects exposed to, or potentially exposed to SARS-CoV-2 virus, or suffering from COVID-19, comprises the step of administering to the human subjects a multiple-component antiviral formulation comprising a curcumin component, harmine component, and isovanillin component, and/or variants thereof. The formulation may also be used to inhibit SARS-CoV-2 virus in cell-based assays or in the manufacture of antiviral medicaments.

21 Claims, 3 Drawing Sheets

(56) References Cited

OTHER PUBLICATIONS

Cooper, "Health benefits of Beta-Sitosterol", healthfully.com/health-benefits-of-beta-sitosterol-6111702.html, 2017.
Moloudizargari, et al., "Pharmacological and therapeutic effects of Peganum harmala and its main alkaloids", Pharmacogn Rev., 2013, 7(14), 199-212.
Office Action in corresponding U.S. Appl. No. 17/540,810, dated Apr. 18, 2023.
Office Action in corresponding U.S. Appl. No. 17/540,766, dated Feb. 2, 2023.
Office Action in corresponding U.S. Appl. No. 17/540,766, dated Jul. 5, 2023.

* cited by examiner

INHIBITION OF COVID-19 VIRUS BY FORMULATIONS CONTAINING CURCUMIN, HARMINE, AND ISOVANILLIN

CROSS-REFERENCE TO RELATED APPLICATIONS

The present application claims the priority benefit of U.S. Provisional Patent Application Ser. No. 63/129,428, filed Dec. 22, 2020, entitled INHIBITION OF COVID-19 VIRUS BY MULTIPLE-COMPONENT FORMULATIONS, incorporated by reference in its entirety herein.

BACKGROUND

Field of the Invention

The present disclosure is broadly concerned with a new medicament for the treatment of SARS-CoV-2 virus, the cause of the ongoing COVID-19 pandemic. More particularly, the disclosure is concerned with the use of multiple-component formulations comprising curcumin, harmine, and isovanillin and variants thereof, as effective agents inhibiting replication of the virus and the resulting COVID-19 disease.

Description of Related Art

The COVID-19 pandemic, also known as the coronavirus pandemic, is an ongoing pandemic of coronavirus disease 2019 (COVID-19) caused by severe acute respiratory syndrome coronavirus 2 (SARS-CoV-2), first identified in December 2019 in Wuhan, China. COVID-19 mainly spreads through the air when people are near each other long enough, primarily via small droplets or aerosols, as an infected person breathes, coughs, sneezes, sings, or speaks. Transmission via fomites (contaminated surfaces) has not been conclusively demonstrated. It can spread as early as two days before infected persons show symptoms (presymptomatic), and from asymptomatic (no symptoms) individuals. People remain infectious for up to ten days in moderate cases, and two weeks or longer in severe cases.

Common symptoms include fever, cough, fatigue, breathing difficulties, and loss of smell and taste. Complications may include pneumonia and acute respiratory distress syndrome. The incubation period is typically around five days but may range from one to 14 days.

The responses have caused global social and economic disruption, including the largest global recession since the Great Depression. It has led to the postponement or cancellation of events, widespread supply shortages exacerbated by panic buying, famines affecting hundreds of millions of people, and decreased emissions of pollutants and greenhouse gases. Educational institutions have been partially or fully closed. Misinformation has circulated through social media and mass media.

In response to these conditions, there has been a tremendous scientific effort to develop both prophylactic vaccines and medication treatments. Despite the development of several vaccines, and emerging treatment protocols, transmission and infection remains high, as the virus mutates into different forms (e.g., so-called Delta and Omicron variants) evading current protocols. Thus, there remains a need in the art for new and effective treatments which inhibit the replication of SARS-CoV-2 virus, reduce viral transmission, and prevent or ameliorate symptoms of COVID-19. There is accordingly a need in the art for new and effective treatments which inhibit the replication of SARS-CoV-2 virus and prevent or ameliorate COVID-19.

SUMMARY OF THE INVENTION

The present disclosure provides improved methods for inhibiting the SARS-CoV-2 virus. In one aspect of the invention, the methods comprise or consist essentially, or even consist of, the use of a multiple-component antiviral formulation demonstrating preclinical synergy between the three components, isovanillin identified in *A. palaestinum*, harmine identified in *Peganum harmala*, and curcumin identified in *Curcuma longa*.

The present disclosure provides important multiple-component antiviral formulations useful for inhibiting SARS-CoV-2 virus and in the treatment of COVID-19 disease. Generally, the formulations comprise respective quantities of a curcumin component, a harmine component, and an isovanillin component and variants thereof, and which may also include additional minor ingredients. The methods involve the administration of the multiple-component antiviral formulations to a subject in prophylactically or therapeutically effective amounts which inhibit replication of the SARS-CoV-2 virus in the subject.

The use of the multiple-component antiviral formulations in the manufacture of a medicament for such treatment is also within the ambit of the invention.

The present disclosure also includes methods of inhibiting viral replication by contacting SARS-CoV-2 virus with the multiple-component antiviral formulations in an effective amount and for an effective period of time in order to inhibit the growth, replication, and/or viability of the virus. Such usages would typically be in vitro.

DETAILED DESCRIPTION OF THE PREFERRED EMBODIMENTS

Methods described herein include those for inhibiting replication of coronavirus, and prevention or amelioration of COVID-19. In one aspect, the methods comprise (consist essentially or even consist of) contacting coronavirus with amounts of a multiple-component antiviral formulation effective to inhibit viral replication for an effective period of time. In another aspect, the methods comprise (consist essentially or even consist of) administering a therapeutically or prophylactically effective amount of the multiple-component antiviral formulations to human subjects in need thereof. The subjects may be at risk of viral infection or exposure to coronavirus and/or may be individuals identified as having been infected with coronavirus. Such individuals may be symptomatic (have symptoms of COVID-19 disease) or asymptomatic (no visible symptoms of COVID-19 disease, but may nonetheless test positive for SARS-Co-V2 virus on a molecular (PCR) or antigen test). Thus, "therapeutic" use of the formulation refers to processes that are intended to produce a beneficial change in an existing condition (e.g., viral infection) of the subjects, such as by reducing the severity of the clinical symptoms and/or effects of the infection, and/or reducing the duration of the infection/symptoms/effects. Likewise, "prophylactic" use of the formulation refers to processes that are intended to inhibit or ameliorate the effects of a future viral infection to which subjects may be exposed (but is not currently infected with). In some cases, the formulations may prevent the development of observable morbidity from viral infection (i.e., near 100% prevention) (e.g., the patient remains asymptomatic even though they may otherwise test positive for the virus). In other cases, the formulations may only partially prevent and/or lessen the extent of morbidity due to the viral infection in a patient testing positive and/or showing symptoms (i.e., reduce the severity of the symptoms and/or effects of the infection, and/or reduce the duration of the infection/symptoms/effects). In either case, the formulations are still considered to "prevent" the target infection. In one or more embodiments, the formulations treat and/or prevent serious illness (e.g., requiring hospitalization and/or oxygen therapy) and/or death. In one or more embodiments, the formulations are particularly suited for reducing the severity of COVID-19 disease in high-risk individuals.

Multiple-Component Formulations

In their broadest aspects, the formulations used in the context of the invention comprise (or consist essentially of, or consist of) individual quantities of a curcumin component, a harmine component, and an isovanillin component, homogenously mixed together as the principal ingredients working synergistically to provide health benefits.

Curcumin (diferuloylmethane, 1,7-bis(4-hydroxy3-methoxyphenyl)-1,6-heptadiene-3,5-dione) is a symmetrical diaryl heptanoid. It occurs as a part of a curcuminoid plant extract containing curcumin, demethoxycurcumin, and bis-demethoxycurcumin.

CAS Number: 458-37-7

Molecular Formula: C21H206
Molecular Weight: 368.39

It exists in solution as an equilibrium mixture of the symmetrical dienone (diketo) and the keto-enol tautomer; the keto-enol form is strongly favored by intramolecular hydrogen bonding.

C-1

Curcumin

Curcumin contains two aryl rings separated by an unsaturated 7-carbon linker having a symmetrical β-diketone group (as used herein, "β-diketone" embraces both tautomeric forms, namely the diketo and enol forms). The aryl rings of curcumin contain a hydroxyl group in the para position and a methoxy group in the meta position.

In one or more embodiments, curcumin components for use in the formulation include curcumin, tetrahydro curcumin, demethyl curcumin, demethoxy curcumin, disdemethoxy curcumin, 1,3-diphenyl-2-propanone, caffeic acid phenethyl ester, (1E,4E)-1,5-bis[3,5-bis(methoxymethoxy)phenyl]-1,4-pentadien-3-one, 1,7-di(1-naphthyl)-2,6-heptanedione, trans,trans-1,5-Bis[4-(trifluoromethyl)phenyl]-1,4-pentadien-3-one, 1,5-dibenzoylpentane, (2E,5E)-2,5-dibenzylidenecyclopentanone, 2,6-bis(4-fluorobenzal)cyclohexanone, (1E,4E)-1,5-bis(4-fluorophenyl)-1,4-pentadien-3-one, FLLL31, and mixtures thereof.

Harmine (7-methoxy-1-methyl-9H-pyrido[3,4-b]indole) is a methoxy methyl pyrido indole belonging to the β-carboline family of compounds.

CAS Number: 441-51-3

Molecular Formula: C13H12N2O
Molecular Weight: 212.25

The chemical structure of harmine, 1-methyl-7-methoxy-β-carboline, is shown as follows:

In one or more embodiments, harmine components for use in the formulation include harmine, harmaline, harmane, hamalol, harmol, norharmane, 6-methoxyharmalan, bromo harmine, 2-methyl harmine, 4,9-dihydro-3H-beta-carbolin-1-yl methyl ether, 1-(4-nitrophenyl)-2,3,4,9-tetrahydro-1H-beta-carboline hydrochloride, 1,2,3,4-tetrahydro-9H-pyrido[3,4-b]indole {THbC}, 1,2,3,4-tetrahydro-beta-carboline-1-carboxylic acid, 6-Methoxy-1,2,3,4-tetrahydro-9H-pyrido[3,4-b]indole, 3-hydroxymethyl-b-carboline, 2,3,4,5-tetrahydro-8-methoxy-1H-pyrido[4,3-b]indole, 6-Methoxy-1,2,3,4-tetrahydro-9H-pyrido[3,4-b]indole-1-carboxylic acid, ethyl b-carboline-3-carboxylate, and mixtures thereof.

Isovanillin (CAS #621-59-0) is a phenolic aldehyde vanillin isomer, and has the molecular formula C8H8O3. The vanillin compound(s) useful in the invention are phenyl aldehydes, and one family of such compounds have the structure where R1 is selected from the group consisting of OH, H, C1-C4 alkoxy groups, F, Cl, Br, I, N, and NO2, and R2 and R3 are independently selected from the group consisting of H, OH, and C1-C4 alkoxy groups, it being understood that the aldehyde group and R1, R2, and R3 can be located at any position around the phenyl ring.

Certain specific vanillin compounds are vanillin, isovanillin (3-hydroxy-4-methoxybenzaldehyde), orthovanillin (2-hydroxy-3-methoxybenzaldehyde), and include the following exemplary vanillin compounds:

vanillin

3-ethoxy-4-hydroxybenzaldehyde 3-ethoxy-2-hydroxybenzaldehyde

2-hydroxy-3-methoxybenzaldehyde 2-hydroxybenzaldehyde

3-hydroxybenzaldehyde 4-hydroxybenzaldehyde

3,4-dihydroxybenzaldehyde 2,3-dihydroxybenzaldehyde

2,4-dihydroxybenzaldehyde 2,5-dihydroxybenzaldehyde 2,3,4-trihydroxybenzaldehyde 3,4,5-trihydroxybenzaldehyde In one or more embodiments, isovanillin components for use in the formulation include isovanillin, orthovanillin, isovanillyl alcohol, isovanillic acid, 2-bromo-3-hydroxy-4-methoxy benzaldehyde, 2-iodo-3-hyroxy-4-methoxy benzaldehyde, o-anisaldehyde, isovanillin oxime, ethyl vanillin, vanillin isobutyrate, veratraldehyde, 5-nitrovanillin, vanillin acetate, 3-benzyloxy-4-methoxybenzaldehyde, 3-hydroxy-5-methoxybenzaldehyde, methyl isovanillate, acetovanillone (apocynin), 2-hydroxy-4-methoxybenzaldehyde, trans-ferulic acid, 3-hydroxy-4-methoxycinnamic acid, caffeic acid, and mixtures thereof.

Thus, as used herein, unless otherwise dictated by the context, "curcumin," "harmine," and "isovanillin" components respectively refer to the above-identified compounds as well as the isomers, tautomers, derivatives, solvates, degradation products, metabolites, esters, metal complexes (e.g., Cu, Fe, Zn, Pt, V), prodrugs, and pharmaceutically acceptable salts thereof. As used herein, a derivative is a compound that can be imagined to arise or actually be synthesized from a parent compound by replacement of one atom with another atom or a group of atoms while at least maintaining the desired degree of pharmacological activity of the parent compound. Similarly, pharmaceutically acceptable salts with reference to the components of the composition means salts which are pharmaceutically acceptable, e.g., salts which are useful in preparing pharmaceutical compositions that are generally safe, non-toxic, and neither biologically nor otherwise undesirable and are acceptable for human pharmaceutical use, and which possess the desired degree of pharmacological activity, and in this case antiviral activity. Such pharmaceutically acceptable salts may include acid addition salts formed with organic or inorganic acids, and base addition salts. In preferred practice, the individual components are naturally or synthetically derived, and should have purities of at least about 90% by weight, and most preferably at least about 98% by weight. As used herein, "synthetically derived" means that the component in question was synthesized using specific starting ingredients and one or more chemical and/or biological reactions to obtain substantially pure compounds. Modification of naturally occurring products may involve extractions, or any other physical or chemical steps to achieve the desired end product, e.g., harmine components may be obtained from treatment of harmala seed, or curcumin components may be obtained from treatment of turmeric. For example, curcumin can be synthetically derived to a high degree of purity. Alternately, curcumin can be obtained by extraction or other treatment of naturally occurring turmeric so that the curcumin content of the modified turmeric has the above-noted levels of curcumin therein.

Generally, it is preferred that the isovanillin component is the preponderant component in the antiviral formulation on a weight basis, with the harmine and curcumin components being present in lesser amounts on a weight basis. Still further, the isovanillin component may be present at a level of at least three times (more preferably at least five times) greater than that of each of the harmine and curcumin components. The as-added amounts of the components should give weight ratios of from about 0.1-25.0:0.1-5:0.1-5 (isovanillin:harmine:curcumin), and more preferably from about 10:1.7:0.85. In terms of amounts of the three components, isovanillin should be present at a level of from about 25-85% by weight, harmine at a level of from about 7-50% by weight, and curcumin at a level of from about 5-40% by weight, all based upon the total weight of the three ingredients taken as 100% by weight.

"Pharmaceutically acceptable salts" with reference to the components means salts of the components which are pharmaceutically acceptable, i.e., salts which are useful in preparing pharmaceutical compositions that are generally safe, non-toxic, and neither biologically nor otherwise undesirable and are acceptable for human pharmaceutical use, and which possess the desired degree of pharmacological activity. Such pharmaceutically acceptable salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts Properties, and Use, P. H. Stahl & C. G. Wermuth eds., ISBN 978-3-90639-058-1 (2008). The compounds may be in crystalline or amorphous forms, and may be lyophilized.

Some or all of the ingredients can be in the form of acceptable esters or salts. The esters and salts should be generally safe, non-toxic, and neither biologically nor otherwise undesirable and are acceptable for human use, and which possess the desired degree of activity. Accordingly, the recitation herein of the ingredients is intended to embrace not only the named ingredients, but also any acceptable esters or salts thereof.

The dosage forms of the invention may be in the form of liquids, gels, suspensions, solutions, or solids (e.g., tablets, pills, or capsules of powdered components). The term "unit dosage form" refers to a physically discrete unit suitable as a unitary dosage for human or animal use. Each unit dosage form may contain a predetermined amount of the multiple component antiviral formulation calculated to produce a desired effect.

In the one or more embodiments, the curcumin component is present at a level of from about 5-40% by weight (preferably about 5-20%, preferably about 7-15%, preferably about 8-13%), the harmine component is present at a level of from about 7-50% by weight (preferably about 7-30%, preferably about 10-20%, preferably about 11-15%), and the isovanillin component is present at a level of from about 25-85% by weight (preferably about 50-85%, preferably about 65-80%, preferably about 70-80%), all of the foregoing based upon the total weight of the combined curcumin, harmine, and isovanillin components taken as 100% by weight. In some cases, the curcumin component, harmine component, and isovanillin component are dispersed in a non-interfering solvent, such as solvents selected from the group consisting of C1-C4 alcohols, DMSO, and mixtures thereof. Alternately, a powdered product may be employed which is a mixture of powdered curcumin, harmine, and isovanillin. The agents may include additional inactive pharmaceutically-acceptable ingredients and/or vehicles as a base carrier composition in which the active ingredients are dispersed. As used herein, the term "pharmaceutically-acceptable" means not biologically or otherwise undesirable, in that it can be administered to a subject without excessive toxicity, irritation, or allergic response, and does not cause any undesirable biological effects or interact in a deleterious manner with any of the other components of the composition in which it is contained. The term "carrier," as used herein, means one or more compatible base compositions with which the active ingredient(s) (e.g., curcumin, harmine, and isovanillin) is combined to facilitate the administration of ingredient(s), and which is suitable for administration to a patient. Such preparations may also routinely contain salts, buffering agents, preservatives, and optionally other therapeutic ingredients. The carrier would naturally be selected to minimize any degradation of the active ingredient and to minimize any adverse side effects in the subject, as would be well known to one of ordinary skill in the art. Pharmaceutically-acceptable ingredients include those acceptable for veterinary use as well as human pharmaceutical use. Exemplary carriers include petrolatum, mineral oil, alcohols (e.g., cetyl alcohol, stearyl alcohol), propylene glycol, nonionic surfactants and/or emulsifiers (e.g., polysorbates), polymers, parabens, silicones, waxes, preservatives, aqueous solutions, and combinations thereof.

GZ17-6.02

One particular multiple-component antiviral formulation in accordance with the invention is referred to as "GZ17-6.02," and used interchangeably herein with "6.02" or "602". This combination comprises 77% by weight of 98% pure solid synthetic isovanillin, 13% by weight of 99% pure solid synthetic harmine, and 10% by weight of a commercially available solid curcumin product containing 99.76% by weight curcuminoids, namely ~71.38% curcumin, ~15.68% demethoxycurcumin, and ~12.70% bisdemethoxycurcumin. The solids (powders) are thoroughly and homogenously mixed together to complete the multiple-component antiviral formulation. Thus, the three-component antiviral formulation consists of a mixture of respective quantities of highly purified curcumin components, harmine components, and isovanillin components at ratios of approximately 0.1-25:0.1-5:0.1-5 (isovanillin:harmine:curcumin). Each such component may be made up of one or more isovanillin, harmine, and/or curcumin compounds, respectively.

The single most preferred GZ17-6.02 antiviral formulation, and that tested in the examples, was made by dispersing relative quantities of solid synthetic isovanillin (771 mg, 98% by weight purity), synthetic harmine (130.3 mg, 99% by weight purity), and a commercially available curcumin product derived by the treatment of turmeric (98.7 mg, containing 99.76% by weight curcuminoids, namely 71.38% curcumin, 15.68% demethoxycurcumin, and 12.70% bisdemethoxycurcumin), at a weight ratio of 771:130.3:98.7 (isovanillin:harmine:curcumin product). Additional details regarding this formulation as a synergistic anticancer agent are described in detail in U.S. Pat. No. 9,402,834, filed May 26, 2015, and U.S. Pat. No. 10,092,550, filed Oct. 28, 2016, each incorporated by reference in its entirety herein, especially as it relates to three-component formulations of isovanillin, harmine, and curcumin.

Use of the Multiple-Component Formulations

The formulations of the invention, in whatever physical form, are designed for administration to subjects exposed, or potentially exposed, to the SARS-CoV-2 virus, or those suffering from the COVID-19 disease. The formulations may be administered in any convenient manner, such as by oral, rectal, nasal, ophthalmic, parenteral (including intraperitoneal, gastrointestinal, intrathecal, intravenous, cutaneous (e.g., dermal patch), subcutaneous (e.g., injection or implant), or intramuscular) routes. In one or more embodiments, the dosage formulations are administered in repeated dosages, e.g., daily, multiple time daily, and the like.

In use, a therapeutically effective amount of the multiple-component antiviral formulation is administered to a mammalian subject in need thereof for a therapeutically effective amount of time. As used herein, a "therapeutically effective" amount refers to the dosage amount and/or duration that will elicit the biological or medical response of a tissue, system, or subject that is being sought by a researcher or clinician, and in particular elicit some desired therapeutic effect as against the coronavirus cells by slowing and/or inhibiting activity, growth, or replication of the cells. One of skill in the art recognizes that an amount or duration may be considered therapeutically "effective" even if the condition is not totally eradicated or prevented, but it or its symptoms and/or effects are improved or alleviated partially or inhibited from worsening in the subject. Such therapeutically effective dosages and durations may comprise a single unit dosage or, more usually, periodic (e.g., daily or weekly) administration of lower dosages over time.

In one or more embodiments, the mammalian subject in need of treatment is a subject having one or more pre-existing conditions or co-morbidities that give the subject a higher risk of serious illness or death due to COVID-19. In one or more embodiments, such pre-existing or underlying health conditions includes, without limitation, one or more of cancer, chronic liver or kidney disease, lung conditions (asthma, COPD, cystic fibrosis), Diabetes, and/or cardiovascular conditions such as heart failure, coronary artery disease, cardiomyopathies, and hypertension. Such subjects are referred to herein as "high risk subjects." In one or more embodiments, administering a therapeutically effective amount of the multiple-component antiviral formulation to a high risk subject may not prevent detection of SARS-Co-V virus or diagnosis of COVID-19 disease based upon symptoms, but will reduce severity and/or duration of symptoms, and in particular will prevent serious illness and/or death.

Levels of dosing to human subjects of the multiple-component antiviral formulations hereof are quite variable owing to factors such as the patient's age, patient's physical condition, and the severity of the disease. In general, however, regardless of the dosage form or route of administration employed, the multiple-component antiviral formulations should be dosed of from about 5 to 2000 mg per day, more usually from about 200 mg to 1,000 mg per day, more usually from about 350 mg to about 800 mg per day, and more preferably from about 450 mg to about 900 mg, and even more usually from about 600 mg to about 900 mg per day (in some cases up to about 750 mg or 800 mg total per day). Such dosages may be based on a single administration per day, but more usually multiple administrations per day.

In one or more embodiments, in solid dosage form, the blended powders should be of a size to pass through a 50-mesh screen while being retained by a 100-mesh screen. Still further, the blended powders are placed in capsules for ease of dosage. The capsules or tablets should each contain from about 5 mg to about 1,000 mg of the blended powders (per capsule or tablet), preferably from about 200 mg to about 500 mg, most preferably from about 300 mg to about 450 mg, preferably from about 350 mg to about 400 mg, and preferably about 375 mg of the blended powders. While such powdered formulations are preferred for ease of manufacture and administration, it should be understood that the invention is not so limited. For example, the blended ingredients may be prepared as liquid dispersions or solutions using appropriate, non-interfering dispersants or solvents; other possible dosage forms include gels, suspensions, or solids such as tablets or pills.

Where the aforementioned capsules are used, the administration would be oral, and the recommended dosage level would be two such capsules per day, taken twice daily, one capsule per serving. In one or more embodiments, the capsules comprise about 375 mg of the multiple-component formulation, which is dosed at two capsules per day (750 mg total daily dose). It will be appreciated that dosing instructions can be adjusted to meet the total recommended daily dosages depending on the size of each capsule. For example, smaller capsules can be used and dosed three times per day to achieve a 750 mg total daily dose, or two capsules twice a day to achieve a 750 mg total daily dose, and the like. Other dosage forms include capsules comprising about 450 mg of the multiple-component formulation, which is dosed at two capsules per day (900 mg total daily dose). Dosage forms may be administered with a meal, or suspended or dissolved in PEPTAMEN® or other fat-containing liquid before administration, or co-administered with such fatty substances. A clinician or researcher may determine the appropriate administration protocol depending upon the dosage form and route of administration used.

The multiple-component antiviral formulations may be administered in conjunction with other recommended therapies for treating COVID-19 or its symptoms. The multiple-component antiviral formulations may also be taken prophylactically, such as during period of time where there is high community transmission of SARS-CoV-2. The methods can be also applied for clinical research and/or study.

Additional advantages of the various embodiments of the invention will be apparent to those skilled in the art upon review of the disclosure herein. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

As used herein, the term "inhibit" refers to a reduction or decrease viral titer or quantity, compared to a baseline. For example, in the context of the present invention, inhibition of viral replication refers to a decrease in amount or speed of viral replication as compared to baseline (e.g., as detected by a rapid antigen test, or molecular/PCR test, or other suitable testing methodology). By comparing a baseline obtained before administration of the formulation to the values obtained from the individual after administration of the formulation, those of ordinary skill in the art can readily determine whether or not viral replication has been inhibited and to what extent. Thus, an "effective amount" to inhibit viral replication refers to the amount of a given formulation that results in a reduced level of viral replication and thus a reduced amount of detectable virus in the individual (e.g., reduced viral titer or viral load) when comparing the baseline detected amount to the reduced amount using the same testing methodology. Preferably, prophylactic and/or therapeutic methods of the invention will lead to a decrease of at least 20%, at least 30%, at least 40%, at least 50%, at least 60%, at least 70%, at least 80%, or even at least 90% as compared to the baseline. Preferably, such reductions are seen within 72 hours after administration, preferably within 48 hours, preferably within 36 hours, more preferably within 24 hours. Correspondingly, such reductions in viral load will advantageously lead to an amelioration, improvement, or decrease in one or more symptoms associated with coronavirus infection and/or reduced transmission of the virus from the infected individual. Alternatively, inhibition or antiviral efficacy can be assessed in vitro.

In one or more embodiments, the formulation will inhibit viral replication by at least 50% in a cell-based assay, preferably by at least 60%, 70%, 80%, or 90% in a cell-based assay. Preferably, the formulation will have a Selectivity Index of greater than 1 and preferably 2 or greater. The Selectivity Index is the ratio of the toxic concentration of a formulation against its effective bioactive amount. In one or more embodiments, the toxic concentration is the dose that leads to 50% cell cytotoxicity in an in vitro cell assay. In one or more embodiments, the bioactive amount is the dose that inhibits viral replication by 90% in a cell assay.

Furthermore, the phrase "and/or," when used in a list of two or more items, means that any one of the listed items can be employed by itself or any combination of two or more of the listed items can be employed. For example, if a formulation is described as containing or excluding components A, B, and/or C, the formulation can contain or exclude A alone; B alone; C alone; A and B in combination; A and C in combination; B and C in combination; or A, B, and C in combination.

EXAMPLES

The following example sets forth methods in accordance with the invention. It is to be understood, however, that this example is provided by way of illustration and nothing therein should be taken as a limitation upon the overall scope of the invention.

Example 1

Preliminary Assay of COVID 19 Using Multiple-Component Formulation

The antiviral activity of a multiple-component formulation, designated as GZ17-6.02, on coronavirus was assessed in vitro using novel coronavirus SARS-CoV-2 isolate USA-WA1/2020 (deposited by the Centers for Disease Control and Prevention). For propagation and experimentation with SARS-CoV-2, we used Vero E6 (ATCC® CRL-1586™) cells maintained in EMEM (Eagle's Minimum Essential Medium) cell culture media (cat #30-2003, ATCC, Manassas, VA, USA) supplemented with 2% or 10% fetal bovine serum (FBS), 100 U/mL penicillin, 100 µg/mL streptomycin, 0.01M HEPES buffer solution, 1 mM sodium pyruvate, 1x non-essential amino acids solution (cat #SH3023801, Thermo Fisher Scientific, Waltham, MA, USA), and 2 mM L-glutamine.

The testing stock solution was prepared by dissolving 1 mg of GZ17-6.02 in 1 ml DMSO (1 mg/ml).

Plated cells were first infected with SARS-CoV2 at a multiplicity of infection (MOI) of 0.001. The test formulation was added during and post-infection. At 72 hours post-infection, the cell monolayers were stained with crystal violet to determine the level of cytopathic effect (CPE). The CPE level was quantified to determine the $IC_{90}$ (dose that inhibited viral replication by 90%). Vero cells were also treated with the test formulations alone for 24 hours to determine the $CC_{50}$ (dose that leads to 50% cell cytotoxicity). After 24 hours of treatment, cell viability was determined by a standard MTS colorimetric assay. Based on the $IC_{90}$ and $CC_{50}$, the Selectivity Index ($CC_{50}/IC_{90}$) could be determined. A higher Selectivity Index indicates that the treatment will, theoretically, be both safter and more effective during in vivo treatment for a given viral infection. The results are in the table below.

TABLE

Antiviral activity

| Test Formulation | $CC_{50}$ (µl/ml) | $IC_{90}$ (µl/ml) | Selectivity Index |
|---|---|---|---|
| GZ17-6.02 | 6 | 3 | 2 |

As can be seen, the GZ17-6.02 has a low toxicity profile, while also showing antiviral activity at low dosages. Overall, it presents an acceptable selectivity index, indicating it would be effective against SARS-CoV-2 infection at low dosages, as well as safe to administer.

Example 2

Evaluation of Multi-Component Formulation as Inhibitor of SARS-CoV-2

The antiviral activity of a multiple-component formulation, designated as GZ17-6.02, on coronavirus was assessed in vitro using novel coronavirus SARS-CoV-2 isolate USA-WA1/2020 (deposited by the Centers for Disease Control and Prevention). For propagation and experimentation with SARS-CoV-2, we used Vero E6 (ATCC® CRL-1586™) cells maintained in EMEM (Eagle's Minimum Essential Medium) cell culture media (cat #30-2003, ATCC, Manassas, VA, USA) supplemented with 2% or 10% fetal bovine serum (FBS), 100 U/mL penicillin, 100 µg/mL streptomycin, 0.01M HEPES buffer solution, 1 mM sodium pyruvate, 1x non-essential amino acids solution (cat #SH3023801, Thermo Fisher Scientific, Waltham, MA, USA), and 2 mM L-glutamine.

The multi-component formulation (GZ17-6.02) was tested at a range of concentrations: 3.3 g/mL, 20 µg/mL, 33 µg/mL, and 50 µg/mL. Negative controls were designated as "Untreated" or "No-compound" for cells demonstrating viral infectivity of the chosen cell line in the absence of treatment compounds, as well as "Uninfected" for cells that were not infected with virus. Positive control was evaluated using a Camostat/E-64d inhibitor cocktail ("C/E") demonstrating inhibition of viral infectivity. "Lysis" control indicates the use of detergent to rupture the cells.

The value indicates the theoretical maximum amount of cytotoxicity that can be achieved. Data obtained following treatment with the compound is expressed as a percentage of the lysis value.

1. Cytotoxicity Assay

The cytotoxicity assay assesses the effect of the compound on cells in comparison to untreated cells (background), a non-toxic inhibitor (Camostat/E64d; "C/E"), and a lysis control (maximum cytotoxicity). Compounds that are toxic to the cell line would have "% Max Cytotoxicity" values that are elevated above Camostat/E64d levels, and can approach levels of the lysis control. Compounds that are not toxic to the cells would have values that are significantly lower than the lysis control and are closer to background levels produced by treatment with Camostat/E64d. This assay was performed three times and values for each treatment group and controls were averaged across assays.

Figure 1:
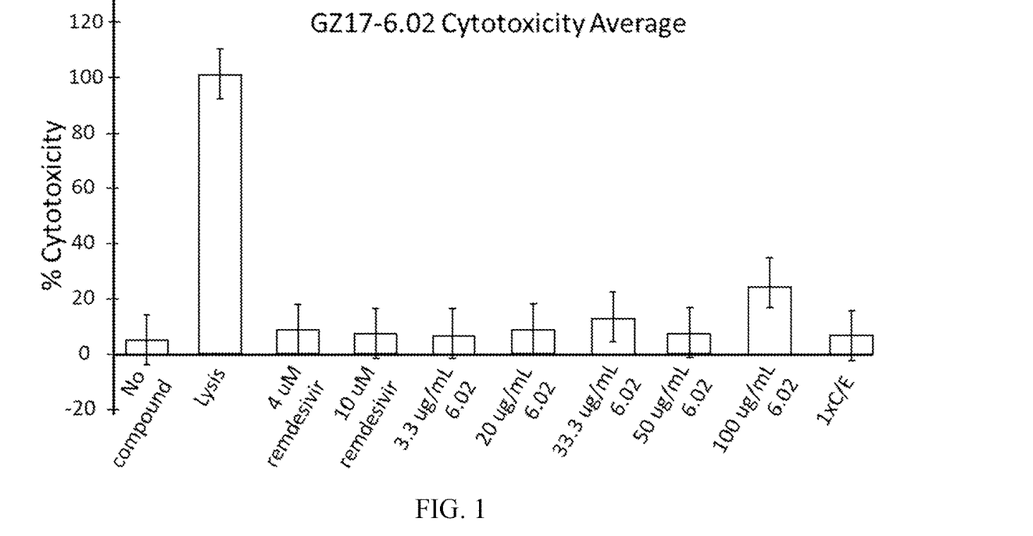
FIG. 1 is a graph showing the averages of the cytotoxicity assay results. The y-axis is the average "% Max Cytotoxicity" measurement for each of the three treatment groups, the controls, and a comparison for the antiviral drug remdesivir, which obtained early FDA approval for use in COVID patients. Error bars are the Standard Deviation.

GZ17-6.02 did not appear to be cytotoxic to the Vero E6 cells even at 50 µg/mL (FIG. 1). While cytotoxicity measurements varied across runs, measurements were far below the max lysis controls, and were generally comparable to the non-toxic 1× C/E control (Student's T-Test results 50 µg/mL 6.02 vs. 1× C/E P>0.05). We did observe some abnormally high cytotoxicity readings on one run with 33 µg/mL 6.02, however that did not recur on subsequent runs, and appears to be an outlier. The cytotoxicity measurements creep up at 100 µg/mL, but are still far lower than the lysis controls. In summary, we believe that 6.02 at 50 µg/mL or lower is not significantly toxic to Vero E6 cells. The data is presented below, with the averages and a comparison to antiviral drug remdesivir also provided in FIG. 1.

|  | No Compound | Lysis | 3.3 µg/mL 6.02 | 20 µg/mL 6.02 | 33.3 µg/mL 6.02 | 50 µg/mL 6.02 | 100 µg/mL 6.02 | 1xC/E |
|---|---|---|---|---|---|---|---|---|
| % Cytotoxicity - Run 1 | | | | | | | | |
| Avg. | 6.248311875 | 100 | 8.3640947 | 14.10822 | 27.9013235 | 12.33456 | 26.4067705 | 9.390474 |
| Stnd. Dev. | 1.102648327 | 21.26068 | 7.3448395 | 13.7311082 | 9.97079067 | 17.47653 | 14.3138627 | 8.967534 |

|  | No Compound | Lysis | 3.3 µg/mL 6.02 | 20 µg/mL 6.02 | 33.3 µg/mL 6.02 | 50 µg/mL 6.02 | 1xC/E |
|---|---|---|---|---|---|---|---|
| % Cytotoxicity - Run 2 | | | | | | | |
| Avg. | 5.453598855 | 100 | 5.336457 | 6.097878433 | 5.72692958 | 6.17597293 | 4.230118443 |
| Stnd. Dev. | 6.704724702 | 7.449832 | 4.74728 | 5.277230966 | 5.85747386 | 2.97475489 | 1.061445555 |

|  | No Compound | Lysis | 3.3 µg/mL 6.02 | 20 µg/mL 6.02 | 33.3 µg/mL 6.02 | 50 µg/mL 6.02 | 1xC/E |
|---|---|---|---|---|---|---|---|
| % Cytotoxicity - Run 3 | | | | | | | |
| Avg. | 5.63523937 | 100 | NA | 6.29820871 | 5.4248741 | 5.51412 | 5.533244087 |
| Stnd. Dev. | 2.239047416 | 7.085372 | NA | 1.72046505 | 3.5084422 | 3.090173 | 1.449137675 |

| — | No Compound | Lysis | 20 ug/mL 6.02 | 33.3 ug/mL 6.02 | 50 ug/mL 6.02 | 1xC/E |
|---|---|---|---|---|---|---|
| | | | % Cytotoxicity - Average | | | |
| Avg. | 5.77905 | 100 | 8.83476906 | 13.0177091 | 8.0082189 | 6.38461234 |
| Stnd. Dev. | 2.961332 | 8.08096424 | 6.16947019 | 3.27106692 | 8.3394863 | 4.45688277 |

2. Virus Plaque Formation Assay

Figure 2:
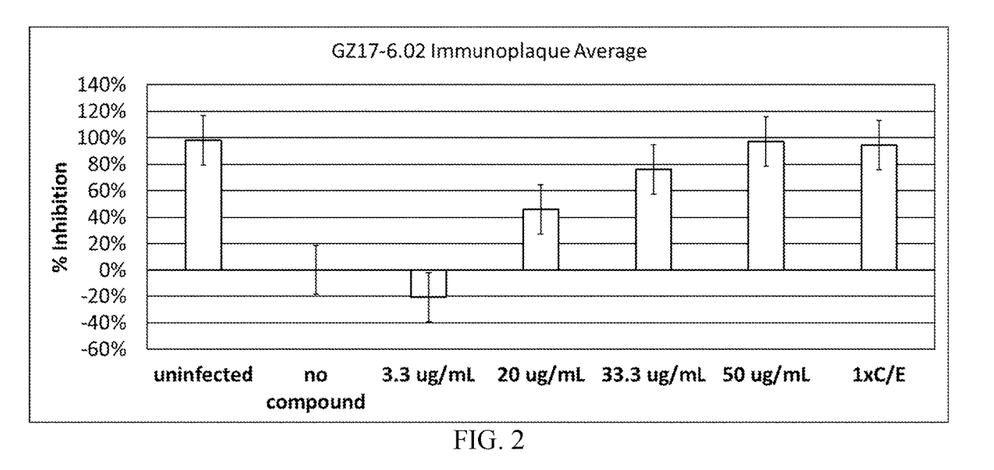
FIG. 2 is a graph showing the summary of three independent run of the virus plaque formation assay. The y-axis is a measure of the inhibition from treatments relative to untreated controls across three replicates. 1XC/E was used as a control. Error bars represent the standard deviation for each experiment. Error bars are the standard deviation.

The virus plaque formation assay measures the ability of a compound to inhibit intercellular spread of the virus and induction of the cytopathic effect. If a compound is effective at inhibiting the virus, "% inhibition" values for an inhibitory compound will be significantly higher than values for the "untreated" control and similar to the values for the "Camostat/E64d" control. If the virus plaquing efficiency is similar to the no compound control, the compound is not inhibiting intercellular spread of the virus under these conditions. This assay was performed three times. FIG. 2 shows the average of the three runs. The data is below.

| — | Uninfected | Untreated (no compound) | 3.3 μg/mL | 20 μg/mL | 33.3 μg/mL | 50 μg/mL | 100 μg/mL | 1xC/E |
|---|---|---|---|---|---|---|---|---|
| | | | % Inhibition - Run 1 | | | | | |
| Avg. | 100% | 0% | 17% | 72% | 91% | 100% | 98% | 97% |

| — | Uninfected | Untreated (no compound) | 3.3 μg/mL | 20 μg/mL | 33.3 μg/mL | 50 μg/mL | 1xC/E |
|---|---|---|---|---|---|---|---|
| | | | % Inhibition - Run 2 | | | | |
| Avg. | 95% | 0% | −8% | 64% | 71% | 95% | 90% |

| — | Uninfected | Untreated (no compound) | 3.3 μg/mL | 20 μg/mL | 33.3 μg/mL | 50 μg/mL | 1xC/E |
|---|---|---|---|---|---|---|---|
| | | | % Inhibition - Run 3 | | | | |
| Avg. | 99% | 0% | −71% | 2% | 67% | 97% | 96% |

As seen from the data, GZ17-6.02 was inhibitory to SARS-CoV-2 plaque formation at 20 μg/mL and higher concentrations (Student's T-Test results: 6.02 vs. Untreated P<0.05 (FIG. 2), and outperformed the positive control at 50 μg/mL. Experimental runs 1, 2 & 3 were performed identically, and no significant difference was observed between the experiments, with the exception of the outliers for 3.3 μg/mL and 20 μg/mL in Run 3.

3. Quantitative RT-PCR for Viral RNA

In parallel with the virus plaque formation assay, viral RNA was extracted from each treatment group, and RNA levels were measured by reverse transcription-polymerase chain reaction, or RTPCR. RT-PCR provides a measure of the effect of the compound on viral multiplication. If the compound inhibits viral multiplication, then "Copy #/L" values for the compound will be significantly lower than the "untreated" control and similar to, or less than, the "C/E" inhibitor control. If the compound does not inhibit viral multiplication, then "Copy #/L" values will be similar to, or greater than, the "untreated" control. Viral RNA extractions are tested with RT-PCR in triplicate, for each treatment, for each run of the virus plaque formation assay.

Figure 3A:
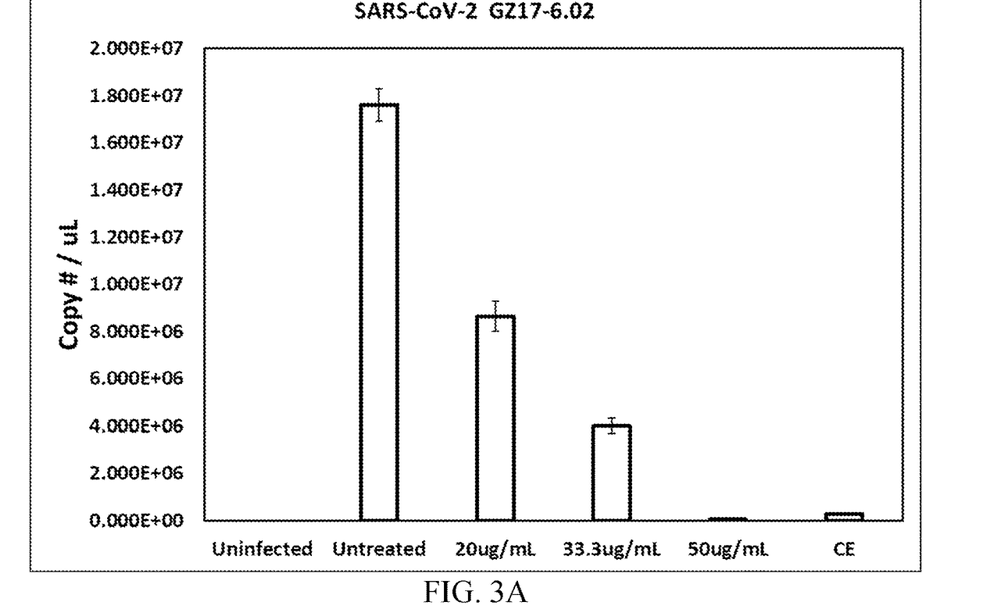
FIG. 3A is a graph showing RNA levels as measured by RT-PCR for each viral plaque formation assay for one test. The y-axis is the copy number of RNA molecules per microliter for the first run. The x-axis lists the three controls and three treatment groups. Error bars are the standard deviation.
Figure 3B:
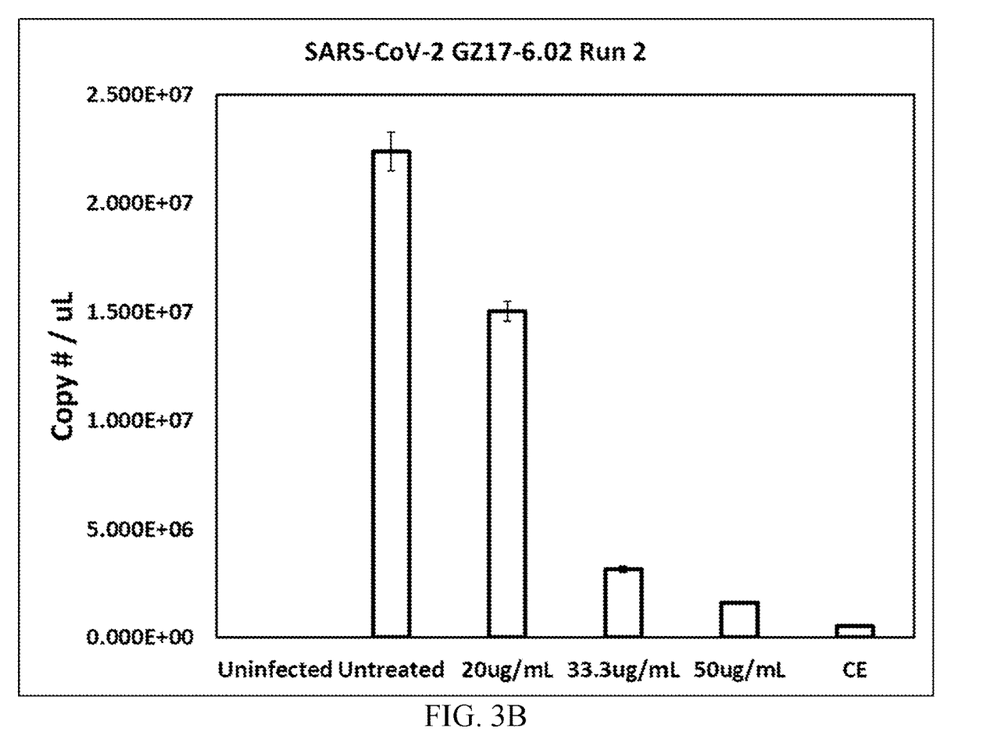
FIG. 3B is a graph showing RNA levels as measured by RT-PCR for each viral plaque formation assay for one test. The y-axis is the copy number of RNA molecules per microliter for the second run. The x-axis lists the three controls and three treatment groups. Error bars are the standard deviation.
Figure 3C:
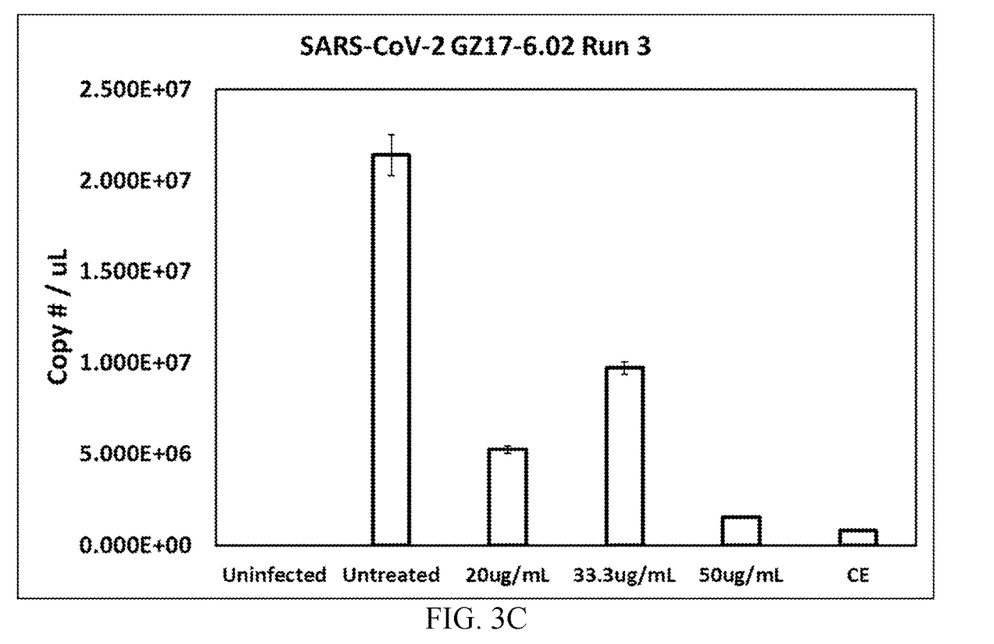
FIG. 3C is a graph showing RNA levels as measured by RT-PCR for each viral plaque formation assay for one test. The y-axis is the copy number of RNA molecules per microliter for the third run. The x-axis lists the three controls and three treatment groups. Error bars are the standard deviation.

FIGS. 3A, 3B, and 3C show the data from the RT-PCR experiments, and these data are comparable to additional experiments that were performed. The results are quite clear. There is a more than 250-fold reduction in viral replication at the 50 μg/mL GZ17-6.02 dosages compared to the untreated control ($61e^3$ vs. $17e^6$ virus copies/μl). These results are consistent with those from the plaque assays above demonstrating that the multiple-component formulation is very effective in inhibiting SARS-Co-V-2 replication at low toxicity levels.

Example 3

In Vivo Antiviral Efficacy in Humans

This example describes antiviral efficacy of GZ17-6.02 against COVID infection in humans. GZ17-6.02 is currently being investigated in a clinical trial as a cancer therapeutic. The study is a Phase 1 trial to evaluate the safety, pharmacokinetics, and pharmacodynamic effects of GZ17-6.02 administered to patients with advanced solid tumors or lymphoma, which have progressed after receiving standard/approved therapy or where there is no approved therapy. GZ17-6.02 is administered orally on a Daily×28 Day Schedule to the patients. The study began before the emergence of COVID-19, and has rolling enrollment of patients. The study has overlapped with the COVID-19 pandemic. Two cancer patients enrolled in the study were diagnosed with COVID-19, coincidentally near or about the time they had also begun their cancer treatments with GC17-6.02. Patient details and outcomes are summarized below.

Patient 021 is a 70-year-old male diagnosed with Renal Cell Carcinoma. The patient had multiple abdominal metastatic lesions. He is a former smoker who also is diagnosed with diverticulosis and GERD and suffers from allergies. The patient began oral administration of GZ17-6.02 on Day 1 at a dose of 450 mg twice daily. One week after his treatment began, the patient tested positive for COVID-19. The patient was quarantined and over the course of his infection the patient reported mild symptoms which soon completely resolved. The patient continued GZ17-6.02 treatment during the course of infection and reported no missed doses during this timeframe. The patient did not receive any other treatments or interventional therapies for the COVID-19 infection.

Patient 025 is a 60-year-old male diagnosed with Non-Small Cell Lung Cancer. The patient had multiple thoracic and hepatic metastatic lesions. He is a non-smoker (never smoked) but also has hypertension. The patient began taking GZ17-6.02 orally on Day 1 at a dose of 375 mg twice daily. Four days after his treatment began, the patient tested positive for COVID-19. The patient was quarantined and over the course of his infection the patient reported mild symptoms which soon completely resolved. The research staff reported that this patient "did quite well through the infection." The patient continued GZ17-6.02 treatment during the course of COVID-19 infection and reported no missed doses during this timeframe. The patient did not receive any other treatments or interventional therapies for the COVID-19 infection.

Notably, the COVID-19 infections in these patients occurred before vaccines had been authorized for use. Neither patient had been vaccinated (at the time) against COVID-19. The favorable outcomes in persons from such high risk groups provide further support, beyond the in vitro testing reported here, that GZ17-6.02 has a therapeutic benefit against COVID-19 infection, even in patients at high risk of death due to COVID (e.g., adults over 65, those with pre-existing conditions, such as cancer, hypertension, smoking, and the like). Moreover, GZ17-6.02 is also well-tolerated by patients, even those in poor health, having a high safety profile and few to no side effects.

The invention claimed is:

1. A method of inhibiting viral replication in a human subject exposed to or at risk of exposure to SARS-COV-2 virus, or suffering from COVID-19, comprising the step of administering to the subject a prophylactically or therapeutically effective amount of a formulation comprising a mixture of curcumin, harmine, and isovanillin, wherein said formulation inhibits replication of said SARS-CoV-2 virus in said subject.

2. The method of claim 1, said formulation being administered to said human subject by a route selected from the group consisting of oral, rectal, nasal, ophthalmic, and parenteral administrations.

3. The method of claim 1, wherein said formulation is administered at a dosage of from about 5 to about 2000 mg per day.

4. The method of claim 1, wherein said human subject is suffering from one or more symptoms of COVID-19 prior to said administration step.

5. The method of claim 1, wherein said human subject is asymptomatic for COVID-19 prior to said administration step.

6. The method of claim 1, wherein said human subject has a baseline amount of detectable SARS-CoV-2 virus prior to said administration step, wherein after said administration step, said baseline amount of detectable virus is reduced.

7. The method of claim 6, wherein the baseline amount of detectable virus is reduced by at least 20% within 72 hours after said administration step.

8. The method of claim 1, wherein said antiviral formulation consists essentially of said curcumin, harmine, and isovanillin.

9. The method of claim 1, wherein said isovanillin is present in a weight ratio of at least 3 times that of each of the harmine and curcumin.

10. The method of claim 1, wherein the isovanillin, harmine, and curcumin are present in a weight ratio of isovanillin:harmine:curcumin ranging from 0.1-25:0.1-5: 0.1-5.

11. The method of claim 10, wherein said weight ratio is about 10:1.7:0.85.

12. The method of claim 10, wherein said weight ratio is 771:130.3:98.7.

13. The method of claim 1, wherein said formulation comprises from about 25-85% by weight isovanillin, about 7-50% by weight harmine, and about 5-40% by weight curcumin, based upon the total weight of the mixture curcumin, harmine, and isovanillin taken as 100% by weight.

14. The method of claim 1, said formulation comprising 77% by weight synthetic isovanillin as said isovanillin, 13% by weight synthetic harmine as said harmine, and 10% by weight curcumin as said curcumin, based upon the total weight of the mixture of isovanillin, harmine, and curcumin taken as 100% by weight.

15. The method of claim 14, wherein said curcumin is from a curcuminoid plant extract containing curcumin, demethoxycurcumin, and bisdemethoxycurcumin.

16. The method of claim 1, wherein said formulation comprises a homogenous mixture of said isovanillin, harmine, and curcumin, and wherein each of said isovanillin, harmine, and curcumin is a solid powder.

17. The method of claim 16, wherein said formulation is administered as a unit dosage form comprising said homogenous mixture in a tablet, capsule, pill, or powdered dispersion.

18. The method of claim 17, wherein said unit dosage form comprises a dosage of from about 200 mg to about 500 mg, wherein said unit dosage form is administered two times per day.

19. The method of claim 1, wherein said formulation is co-administered with a meal, or suspended or dissolved in a fat-containing liquid before administration, or co-administered with a fat-containing liquid.

20. The method of claim 1, wherein said human subject is a high-risk patient having one or more pre-existing conditions making said human subject susceptible to severe illness or death from COVID-19, wherein said formulation reduces the duration and/or severity of symptoms of COVID-19 in said human subject.

21. A method of inhibiting SARS-CoV-2 viral replication in vitro, comprising the step of contacting said virus with an effective amount of a formulation comprising a mixture of curcumin, harmine, and isovanillin, wherein said formulation inhibits replication of said SARS-CoV-2 virus.

* * * * *